United States Patent [19]

Yoshihashi

[11] Patent Number: 4,750,475
[45] Date of Patent: Jun. 14, 1988

[54] OPERATING INSTRUMENT GUIDE MECHANISM FOR ENDOSCOPE APPARATUS

[75] Inventor: Tokusaburo Yoshihashi, Ichikawa, Japan

[73] Assignee: Kabushiki Kaisha Machida Seisakusho, Tokyo, Japan

[21] Appl. No.: 892,832

[22] Filed: Aug. 1, 1986

[30] Foreign Application Priority Data

Aug. 14, 1985 [JP] Japan .......................... 60-124039[U]

[51] Int. Cl.$^4$ .............................................. A61B 1/00
[52] U.S. Cl. ...................................................... 128/6
[58] Field of Search ........................ 128/3, 4, 5, 6, 7

[56] References Cited

U.S. PATENT DOCUMENTS

| 1,127,948 | 2/1915 | Wappler | 128/7 |
| 4,598,698 | 7/1986 | Siegmund | 128/4 |
| 4,655,219 | 4/1987 | Petruzzi | 128/6 X |
| 4,705,023 | 11/1987 | Arai | 128/4 |

FOREIGN PATENT DOCUMENTS 58-20245 4/1983 Japan .

Primary Examiner—William H. Grieb
Attorney, Agent, or Firm—Kane, Dalsimer, Sullivan, Kurucz, Levy, Eisele and Richard

[57] ABSTRACT

An endoscope apparatus comprises an endoscope and an elongated operating instrument adapted to be inserted into the endoscope. The endoscope includes an inserting portion extending from an operating body and adapted to be inserted into a body cavity. A guide tube is provided on the operating body so as to communicate with a guide channel formed through the operating body and the inserting portion. The operating instrument is inserted from the guide tube into the guide channel while being guided by the guide tube, so that a distal end of the operating instrument projects from the guide channel into the body cavity. The guide tube has a bent configuration and is supported on the operating body for turning movement relative thereto.

9 Claims, 4 Drawing Sheets

OPERATING INSTRUMENT GUIDE MECHANISM FOR ENDOSCOPE APPARATUS

BACKGROUND OF THE INVENTION

The present invention relates to an endoscope apparatus and, more particularly, to a guide mechanism for guiding an operating instrument into an endoscope to perform an operation such as, for example, a collection of a tissue from a body cavity of a subject.

In a conventionally general endoscope apparatus as disclosed in Japanese Utility Model Publication No. 58-20245, which can perform an operation such as a collection of a tissue from a body cavity, a flexible inserting portion extends from one end of an operating body, and an ocular portion is provided at the other end of the operating body. A straight guide tube is fixedly mounted on an upper portion of the operating body so as to project therefrom upwardly. A guide channel communicating with the guide tube is formed through the operating body and the inserting portion.

With the endoscope apparatus constructed as described above, the inserting portion is inserted into the body cavity, and an interior of the body cavity is viewed at the ocular portion through an objective optical system provided at a distal end of the inserting portion. When a morbid part is found, a tissue is collected, for example. Specifically, an elongated operating instrument having at a distal end thereof a pair of forceps is inserted from the guide tube into the guide channel so as to have the forceps projecting from the guide channel. The forceps are remotely controlled by an operation of an operating mechanism provided at a proximal end of the operating instrument, to allow the forceps to bite off a tissue from the morbid part.

In the above-described endoscope apparatus, it is often necessary or desirable to turn the operating body to turn the inserting portion around its longitudinal axis, to thereby alter the orientation of the inserting portion within the body cavity. The turning movement of the operating body remarkably affects the insertion and operation of the operating instrument. More particularly, when an operating surgeon holds the operating body in his natural attitude, the guide tube is oriented upwardly and, accordingly, it is easy for the operating surgeon to perform the insertion of the operating instrument into the guide tube and the operation of the operating instrument. However, when the operating body is turned to turn the inserting portion around its longitudinal axis, the position and orientation of the guide tube vary. Therefore, an unnatural attitude would sometimes be forced on the operating surgeon when he inserts the operating instrument into the guide tube or when he operates the operating instrument. This would render the operation by the operating surgeon troublesome.

OBJECT AND SUMMARY OF THE INVENTION

An object of the present invention is to provide an endoscope apparatus which facilitates an insertion and operation of an operating instrument even when an operating body is turned.

According to the present invention, there is provided an endoscope apparatus comprising:

an endoscope including an operating body, an inserting portion extending from the operating body and adapted to be inserted into a body cavity, and at least one guide channel extending through the operating body and the inserting portion;

an elongated operating instrument adapted to be inserted into the guide channel so as to have a distal end projecting from the guide channel into the body cavity; and guide means for guiding insertion of the operating instrument into the guide channel, the guide means comprising at least one guide tube mounted on the operating body so as to communicate with the guide channel, the guide tube having a bent configuration and being supported on the operating body for turning movement relative thereto.

DETAILED DESCRIPTION

The invention will now be described in detail, by way of example, with reference to the drawings.

Figure 1:
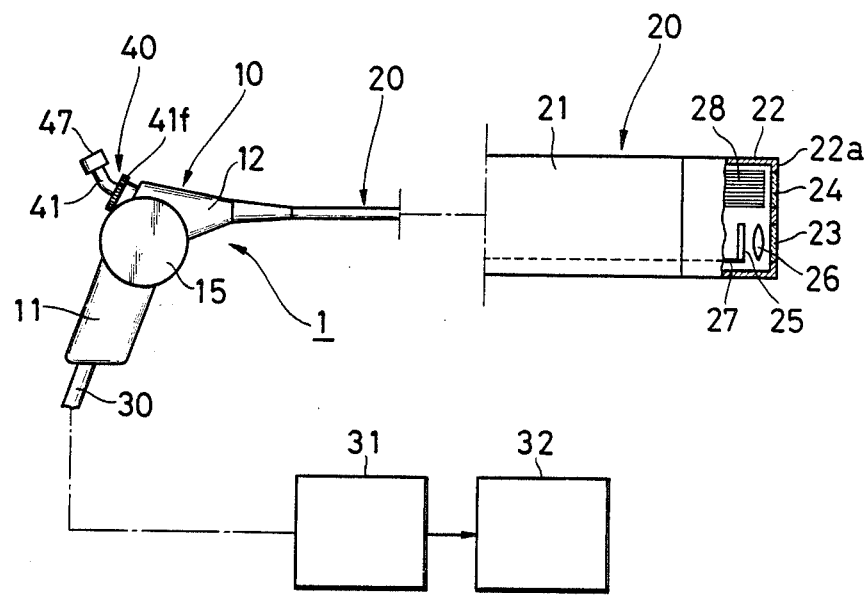
FIG. 1 is a schematic view showing an endoscope apparatus comprising an endoscope and accessories therefore, in accordance with an embodiment of the invention.
Figure 3:
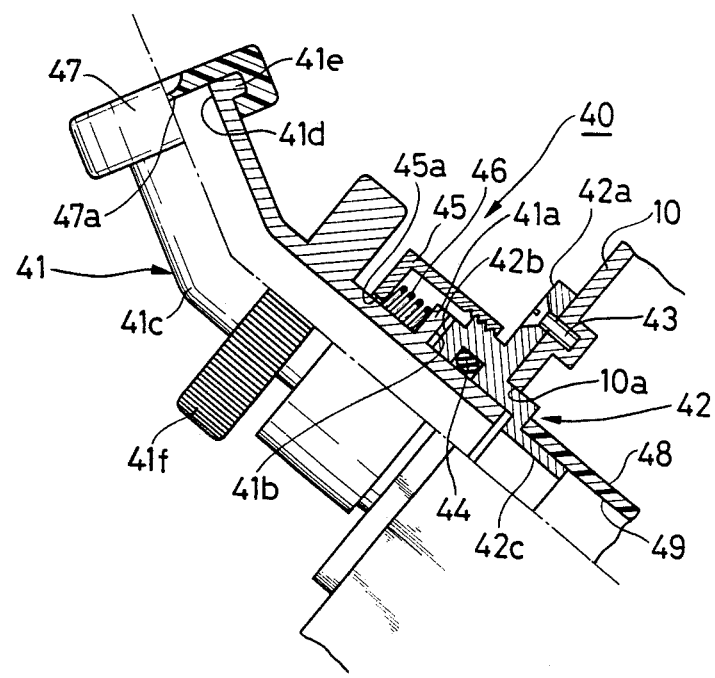
FIG. 3 is an enlarged fragmental, partially cross-sectional view showing an operating instrument guide mechanism incorporated in the endoscope shown in FIGS. 1 and 2.
Figure 2:
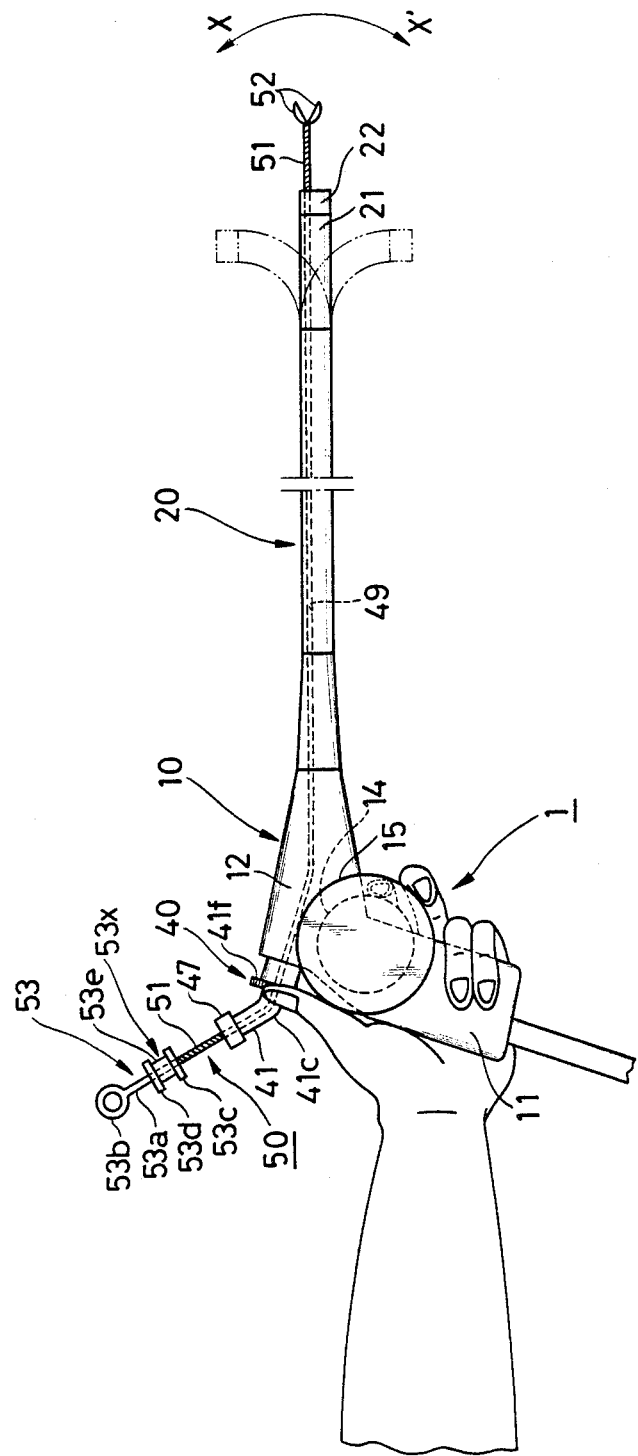
FIG. 2 is a side elevational view showing the endoscope shown in FIG. 1 held with an operating surgeon's left hand.

FIGS. 1 through 6 illustrate an endoscope apparatus in accordance with an embodiment of the invention. As shown in FIG. 2, the endoscope apparatus comprises an endoscope 1 and an elongated operating instrument 50 which is, in use, inserted into the endoscope 1. An overall construction of the endoscope 1 will first be outlined with reference to FIGS. 1 and 2. The endoscope 1 includes an operating body 10 which is generally in the form of a gun comprised of a grip 11 and a support section 12 extending forwardly from an upper end of the grip 11. An inserting portion 20 extends from an end of the support section 12 remote from the grip 11. The inserting portion 20 is flexible and has a bendable section 21 at a distal end of the inserting portion 20 and a hard or rigid tip component 22 at a distal end of the bendable section 21. The grip 11 has its longitudinal axis which intersects a longitudinal axis of the inserting portion 20 and which is inclined downwardly and away from the distal end of the inserting portion 20.

Figure 4:
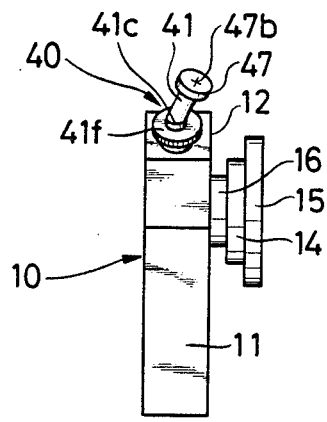
FIGS. 4, 5 and 6 are end views respectively illustrating turning adjustments of a guide tube shown in FIG. 3 in accordance with different turned conditions of an inserting portion.

The grip 11 has mounted thereon two operating dials 14 and 15 which, as shown in FIG. 4, are supported on a hub 16 formed on an upper side surface of the grip 11, in coaxial relation to each other, in such a manner that the operating dials 14 and 15 can be turned around an axis of the hub 16. The operating dials 14 and 15 are connected to the bendable section 21 through respective force transmission mechanisms each including a pair of operating wires, to operate the bendable section 21 so as to variably curve the same.

As shown in FIG. 1, the tip component 22 has an end face 22a provided therein with a viewing window 23 and an illuminating window 24. The tip component 22 has disposed therewithin a solid state image pickup element or image sensor 25 which is optically connected to the viewing window 23 through an objective optical system 26 and to which a signal line 27 is connected. The illuminating window 24 is optically connected to an end face of an optical fiber bundle 28.

A cable 30 has on end thereof connected to a lower end of the grip 11 and the other end connected to a processor unit 31 which has incorporated therein a scanning control circuit and a light source. The scanning control circuit is electrically connected to the image sensor 25 through the aforesaid signal line 27. The light source is optically connected to the illuminating window 24 through the aforesaid optical fiber bundle 28. The signal line 27 and the optical fiber bundle 28 extend to the processor unit 31 through the inserting portion 20, operating body 10 and cable 30. The processor unit 31 is connected to an image receiver 32 such as a CRT display.

An operating instrument guide mechanism 40, by which the present invention is characterized, for guiding the insertion of the operating instrument 50 into the endoscope 1 to be described later, is provided on an end of the operating body 10 opposite to an end thereof from which the inserting portion 20 extends. As shown in detail in FIG. 3, the guide mechanism 40 comprises a guide tube 41 which is supported on the operating body 10 by means of a support ring 42 for turning movement relative thereto. Specifically, the operating body 10 has formed therein an inserting bore 10a through which the support ring 42 is inserted. A flange 42a extending outwardly from an outer periphery of the support ring 42 abuts against an outer surface of the operating body 10 and is fastened thereto by means of screws 43, so that the support ring 42 is fixedly mounted on the operating body 10. The guide tube 41 has a base end thereof inserted into the support ring 42 for turning movement relative thereto. An annular seal member 44 is interposed between the guide tube 41 and the support ring 42 to provide a fluid tightness therebetween.

A cup-shaped cover 45 is threadedly engaged with the outer periphery of the support ring 42. The cover 45 has a bottom wall having formed therethrough an inserting bore 45a through which the guide tube 41 extends. A coil spring 46 is interposed between the bottom wall of the cover 45 and a flange 41a extending outwardly from an outer periphery of the guide tube 41, to resiliently urge the flange 41a against an end face of the support ring 42, to thereby prevent the guide tube 41 from comming out of the support ring 42.

The flange 41a of the guide tube 41 has an end face having formed thereon a daisy seat 41b which has an annular configuration in plan and which has a plurality of radially extending teeth and grooves arranged alternately. The daisy seat 41b of the flange 41a is in mesh with a similar daisy seat 42b on an end face of the support ring 42 to prevent the guide tube 41 from being angularly moved relative to the support ring 42 accidentally or unintentionally.

The guide tube 41 is bent at an intermediate portion 41c thereof, and has a free end opening 41d closed by a rubber cap 47. The cap 47 is snap-fitted on an annular projection 41e formed on the outer periphery of the free end of the guide tube 40. The cap 47 has a central portion 47a which has a relatively thin wall thickness and which has a cruciform cut 41b formed therein as shown in FIG. 4. An operating dial 41f is intergrally formed around a portion of the guide tube 41 which is located between the bent central portion 41c thereof and the operating body 10.

The support ring 42 has a tubular portion 42c which projects into the operating body 10 and to which is connected one end of a guide tube 48 defining a guide channel 49 extending through the operating body 10 and the inserting portion 20 as shown in FIG. 2. The guide tube 48 extends through the operating body 10 and the inserting portion 20 and has the other end connected to an opening (not shown) formed in the end face 22a of the inserting portion 20.

As shown in FIG. 2, the aforementioned elongated operating instrument 50 to be inserted into the endoscope 1 comprises a flexible helical tube 51, a pair of forceps 52 at a distal end of the helical tube 51 and a operating mechanism 53 at a proximal end of the helical tube 51. The pair of forceps 52 are generally in the form of a semi-spherical shell and are adapted to be opened and closed by a linkage (not shown). The operating mechanism 53 includes a hollow shaft 53a having one end thereof having a ring 53b connected thereto and the other end having the helical tube 51 connected thereto. a slider 53x is slidably mounted on the shaft 53a and has flanges 53c and 53d and a tubular section 53e extending between the flanges 53c and 53d to connect them to each other. A wire (not shown) is inserted into the helical tube 51 and has one end connected to the aforesaid linkage and the other end extending through the shaft 53a and connected to the slider 53x.

The operation of the endoscope apparatus constructed as described above will now be described. An operating surgeon holds the grip 11 of the endoscope 1 with his left hand, and inserts the inserting portion 20 into a body cavity of a subject, for example, from his mouth into his stomach. Light from the light source within the processor unit 31 passes through the optical fiber bundle 28 and is irradiated from the illuminating window 24 into the body cavity. Light reflected from an inner wall surface of the body cavity passes through the viewing window 23 and the objective optical system 26 and is received by the image sensor 25, so that an image of the inner wall surface of the body cavity is imaged on a light receiving surface of the image sensor 25.

The image sensor 25 photoelectrically transduces the image to generate a picture signal. The scanning control circuit within the processor unit 31 receives the picture signal from the image sensor 25 and sends the picture signal to the image receiver 32. As a result, the image of the inner wall surface of the body cavity is projected on the image receiver 32. The operating surgeon operates the endoscope 1 while watching the image receiver 32, to view the interior of the body cavity.

The operating surgeon grasps the grip 11 of the endoscope 1 with a so-called ordinary grip in a manner similar to that in which one holds a gun, as shown in FIG. 2. The operating surgeon causes the grip 11 to abut against the palm of his hand and supports the grip 11 with his ring and little fingers. The turning movement of the operating dial 14 with the operating surgeon's thumb and middle finger is transmitted to the bendable section 21 through the operating wires, to cause the bendable section 21 to be curved in a direction indicated by the arrows X—X'. In addition, the turning of the other operating dial 15 with the operating surgeon's thumb and forefinger causes the bendable section 21 to be curved in a direction perpendicular to the direction indicated by the arrows X—X'.

When it is desired to alter the direction or orientation of the inserting portion 20 within the body cavity, the operating surgeon twists his forearm, with the grip 11 being grasped in the manner described above, to turn the inserting portion 20 around its longitudinal axis.

When a morbid part is found during the viewing or observation, the operating surgeon holds the operating instrument 50 with his right hand and inserts the operating instrument 50 through the cut 47b in the cap 47 of the guide mechanism 40 into the guide tube 41, and through the guide channel 49 to allow the distal end of the operating instrument 50 to project into the body cavity from the end face 22a of the inserting portion 20. Thus, the guide tube 41 serves to guide the insertion of the operating instrument 50 into the guide channel 49. Then, the operating surgeon moves the forceps 52 to the morbid part. At the operating mechanism 53, the operating surgeon inserts the thumb of his right hand into the ring 53b and inserts the forefinger and middle finger into between the flanges 53c and 53d with the tubular section 53e being positioned between the forefinger and middle finger. Then, the slider 53x is pulled toward the ring 53b to close the forceps 52 through the wire and likage, to thereby bite off a tissue of the morbid part. Subsequently, with the operating mechanism 53 being held with the operating surgeon's right hand, he pulls the operating instrument 50 out of the endoscope 1.

The turning adjustment of the guide tube 41 of the guide mechanism 40 will now be described. The turning adjustment of the guide tube 41 is performed by the turning of the dial 41f. Upon the turning of the dial 41f, the guide tube 41 is slightly moved axially against the biasing force of the coil spring 46 to allow the teeth of the daisy seat 41b on the guide tube 41 to climb over the teeth of the daisy seat 42b on the support ring 42.

As shown in FIG. 4, under the condition that the grip 11 is not turned, the guide tube 41 is directed or oriented rightward obliquely upwardly. Under this conditions, it is easy for the operating surgeon to insert the operating instrument 50 into the guide tube 41 with the instrument 50 being held with his right hand, and it is also easy for the operating surgeon to operate the operating mechanism 53 to remotely control the forceps 52.

Figure 5:
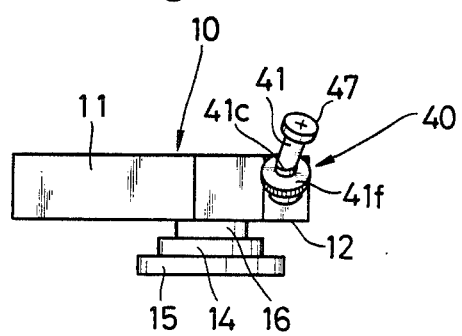

When the operating body 10 is turned in the clockwise direction through 90 degrees, if the guide tube 41 is maintained in the annular relation to the operating body 10 shown in FIG. 4, the guide tube 41 would be directed rightward obliquely downwardly. Then, it would be difficult for the operating surgeon to insert and operate the operating instrument 50, and an unnatural attitude would be forced on the operating surgeon. In this case, as shown in FIG. 5, the guide tube 41 ia angularly moved or turned in the counterclockwise direction relative to the operating body 10 to direct the guide tube 41 rightward obliquely upwardly, to thereby facilitate the insertion and operation of the operating instrument 50.

Figure 6:
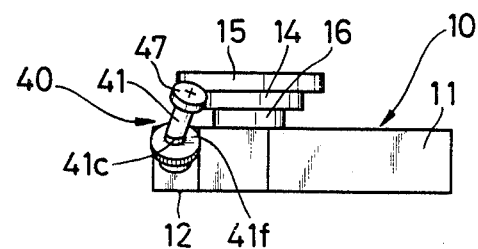

Furthermore, when the operating body 10 is turned in the counterclockwise direction, as shown in FIG. 6, the guide tube 41 is turned in the clockwise direction relative to the operating body 10, to direct the guide tube 41 rightward obliquely upwardly.

Additionally, if the operating surgeon holds the endoscope 1 and an assistant operates the operating instrument 50, the guide tube 41 is turned and adjusted so as to facilitate the operation by the assistant, i.e., such that the guide tube 41 is always directed leftward obliquely upwardly.

Figure 7:
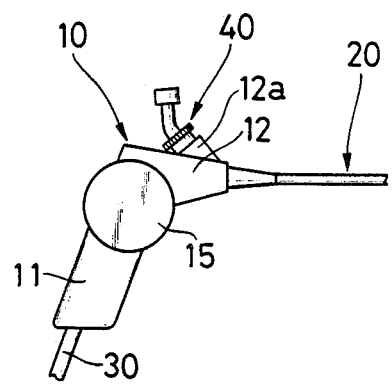
FIG. 7 is a fragmental side elevational view of an endoscope apparatus in accordance with another embodiment of the invention.

FIG. 7 shows an endoscope apparatus in accordance with another embodiment of the invention, in which a projection 12a is formed adjacent the end of the support section 12 from which the inserting portion 20 extends, and the operating instrument guide mechanism 40 is associated with the projection 12a. The embodiment shown in FIG. 7 is similar in other respects to the embodiment described with reference to FIGS. 1 through 6. In FIG. 7, like reference numerals are used to designate like or similar parts and components shown in FIG. 1, and the description of such similar parts and components will therefore be omitted to avoid repetition.

Figure 8:
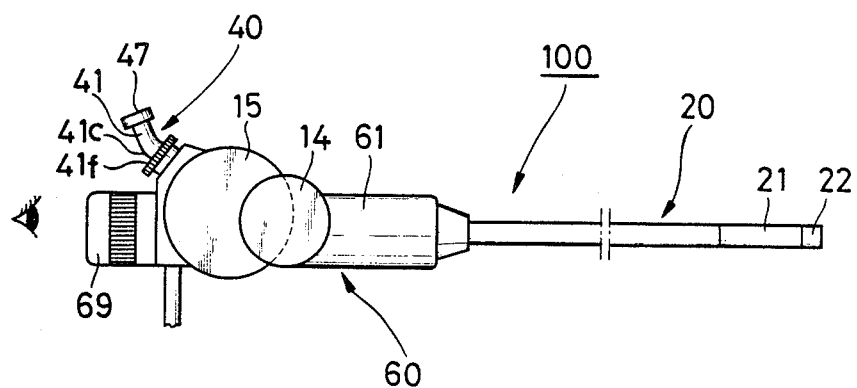
FIG. 8 is a fragmental side elevational view showing an endoscope apparatus in accordance with still another embodiment of the invention.

FIG. 8 shows an endoscope apparatus in acordance with still another embodiment of the invention, in which the operating instrument guide mechanism 40 described with reference to FIGS. 1 through 6 is applied to an endoscope 100 which is of the type widely used conventionally. Specifically, the endoscope 100 comprises an operating body 60 having a grip 61 and an ocular portion 69 in coaxial relation to the inserting portion 20. The ocular portion 69 is provded at an end of the operating body 60 opposite to an end thereof from which the inserting portion 20 extends. The ocular portion 69 has provided therein an ocular optical system which is optically connected to a viewing window and an objective optical system similar to those 23 and 26 shown in FIG. 1, through an image transmission optical system comprised of an optical fiber bundle. In FIG. 8, like reference numerals are used to designate like or similar parts and components shown in FIG. 1, and the description of such like or similar parts and components will therefore be omitted for simplification.

Although the embodiments of the present invention have been described as having a single guide tube 41 and a single guide tube 48 or guide channel 49, the present invention should not be limited to these particular embodiments, but may have a pluraltiy of such guide tubes and guide channels.

Moreover, the operating instrument 50 guided by the guide mechanism 40 has been described as having the forceps 52, but may have injection needles or brushes for resecting a tissue of the inner wall of the body cavity in substitution for the forceps 52.

As described above, with the endoscope apparatus in accordance with the present invention, when the operating body is turned to turn the inserting portion around its longitudinal axis, the guide tube having the curved configuration is turned correspondingly to the turning direction and angle of the operating body, to adjust the angle of the guide tube relative to the operating body. Thus, it is made possible to facilitate the insertion and operation of the operating instrument.

What is claimed is:

1. An endoscope apparatus comprising:
    an endoscope including an operating body, an inserting portion extending from said operating body and adapted to be inserted into a body cavity, and at least one guide channel extending through said operating body and said inserting portion;
    an elongated operating instrument adapted to be inserted into said guide channel so as to have a distal end projecting from said guide channel into the body cavity; and guide means for guiding the insertion of said operating instrument into said guide channel, said guide means comprising at least one guide tube mounted on said operating body so as to communicate with said guide channel, said guide tube having a bent configuration in which said guide tube is composed to a first end portion having a first axis and a second end portion connected to said first end portion and having a second axis extending at an angle to the first axis of said first end portion, said first end portion being supported on said operating body for turning movement relative to thereto about the first axis of said first end portion.

2. An endoscope apparatus as defined in claim 1, wherein said guide tube is located at an end of said operating body opposite to an end thereof from which said inserting potion extends.

3. An endoscope apparatus as defined in claim 1, wherein said guide tube is located adjacent an end of said operating body from which end said inserting portion extends.

4. An endoscope apparatus as defined in claim 1, wherein said operating body is generally in the form of a gun having a grip and a support section connected thereto so as to project therefrom, said grip having a longitudinal axis extending at an angle with respect to a longitudinal axis of said inserting portion, said inserting portion extending from an end of said support section remote from said grip.

5. An endoscope apparatus as defined in claim 4, wherein said guide tube is located at an end of said support section opposite to said end thereof from which said inserting portion extends.

6. An endoscope apparatus as defined in claim 4, wherein said guide tube is located adjacent said end of said support section from which end said inserting portion extends.

7. An endoscope apparatus as defined in claim 1, wherein said operating body has a grip and an ocular portion in coaxial relation to said inserting portion, said inserting portion extending from an end of said grip remote from said ocular portion, said guide tube being located adjacent an end of said grip opposite to said end thereof from which said inserting portion extends.

8. An endoscope apparatus as defined in claim 1, wherein said guide means includes means for preventing said guide tube from being unintentionally turned relative to said operating body.

9. An endoscope apparatus comprising:

an endoscope including an operating body, an inserting portion extending from said operating body and adapted to be inserted into a body cavity, and at least one guide channel extending through said operating body and said inserting portion;

an elongated operating instrument adapted to be inserted into said guide channel so as to have a distal end projecting from said guide channel into the body cavity; and guide means for guiding the insertion of said operating instrument into said guide channel, said guide means comprising at least one guide tube mounted on said operating body so as to communicate with said guide channel, said guide tube having a bent configuration and being supported on said operating body for turning movement relative thereto, said guide means further including means for preventing said guide tube from being unintentionally turned relative to said operating body;

said preventing means comprising a support ring fixedly mounted on said operating body, said guide tube extending through said support ring for turning movement relative thereto, a plurality of teeth provided on said support ring, a plurality of teeth provided on said guide tube and in mesh with said teeth on said support ring, and resilient means associated with said guide tube for resiliently biasing the same toward said support ring to bring teeth on said guide tube into engagement with said teeth on said support ring.

* * * * *